(12) United States Patent
Karolchyk

(10) Patent No.: US 10,561,607 B2
(45) Date of Patent: *Feb. 18, 2020

(54) PHARMACEUTICAL COMPOSITIONS COMPRISING GELS AND METHODS FOR FABRICATING THEREOF

(71) Applicant: Harrow IP, LLC, Nashville, TN (US)

(72) Inventor: John Scott Karolchyk, Lake Hopatcong, NJ (US)

(73) Assignee: Harrow IP, LLC, Nashville, TN (US)

( * ) Notice: Subject to any disclaimer, the term of this patent is extended or adjusted under 35 U.S.C. 154(b) by 12 days.

This patent is subject to a terminal disclaimer.

(21) Appl. No.: 15/395,830

(22) Filed: Dec. 30, 2016

(65) Prior Publication Data

US 2017/0105931 A1 Apr. 20, 2017

Related U.S. Application Data

(62) Division of application No. 14/719,157, filed on May 21, 2015.

(60) Provisional application No. 62/002,711, filed on May 23, 2014.

(51) Int. Cl.
| | |
|---|---|
| A61K 9/00 | (2006.01) |
| A61K 9/06 | (2006.01) |
| A61K 47/10 | (2017.01) |
| A61K 38/14 | (2006.01) |
| A61K 31/7036 | (2006.01) |
| A61K 47/34 | (2017.01) |
| A61K 45/06 | (2006.01) |
| A61K 31/5377 | (2006.01) |
| A61K 31/5575 | (2006.01) |

(52) U.S. Cl.
CPC ............. *A61K 9/0048* (2013.01); *A61K 9/06* (2013.01); *A61K 31/5377* (2013.01); *A61K 31/5575* (2013.01); *A61K 31/7036* (2013.01); *A61K 38/14* (2013.01); *A61K 45/06* (2013.01); *A61K 47/10* (2013.01); *A61K 47/34* (2013.01)

(58) Field of Classification Search
USPC .......................................................... 424/427
See application file for complete search history.

(56) References Cited

U.S. PATENT DOCUMENTS

| | | | |
|---|---|---|---|
| 6,037,328 A | 3/2000 | Hu et al. | |
| 7,842,714 B2 | 11/2010 | Farnes et al. | |
| 8,541,413 B2 | 9/2013 | Wong | |
| 2002/0193370 A1 | 12/2002 | Cagle et al. | |
| 2008/0114076 A1 | 5/2008 | Asgharian et al. | |
| 2008/0132444 A1* | 6/2008 | Li ...................... | A61K 9/0048 424/488 |
| 2009/0082337 A1 | 3/2009 | Venkastesh et al. | |
| 2010/0130550 A1 | 5/2010 | Aberg et al. | |
| 2013/0065888 A1* | 3/2013 | Cetina-Cizmek .... | A61K 9/0048 514/226.5 |
| 2013/0189369 A1* | 7/2013 | Marsh .................. | A61K 47/34 424/497 |
| 2013/0267591 A1 | 10/2013 | Khopade et al. | |
| 2015/0335704 A1 | 11/2015 | Karolchyk | |
| 2017/0112936 A1 | 4/2017 | Karolchyk et al. | |

FOREIGN PATENT DOCUMENTS

| | | | | |
|---|---|---|---|---|
| EP | 1688144 A1 | 8/2006 | | |
| WO | 9001933 A1 | 3/1990 | | |
| WO | 9607406 A1 | 3/1996 | | |
| WO | 2007124476 A2 | 11/2007 | | |
| WO | WO-2014041485 A1 * | 3/2014 | ........... | A61K 9/0051 |

OTHER PUBLICATIONS

Vijaykumar Sutariya et al. (Pharmaceutical Development and Technology, vol. 18, 2013, Issue 4, pp. 957-962).*

* cited by examiner

*Primary Examiner* — Johann R Richter
*Assistant Examiner* — Courtney A Brown
(74) *Attorney, Agent, or Firm* — Wagenknecht IP Law Group PC

(57) ABSTRACT

Pharmaceutical compositions are described, the compositions comprising a therapeutically effective quantity of an active component and a quantity of a sterile gel. Methods for fabricating the compositions and using them for ophthalmic or burn-treating applications are also described.

8 Claims, No Drawings

PHARMACEUTICAL COMPOSITIONS COMPRISING GELS AND METHODS FOR FABRICATING THEREOF

CROSS REFERENCE TO RELATED APPLICATIONS

This application is a divisional under 35 U.S.C. §§ 120 and 121 of U.S. application Ser. No. 14/719,157 filed on May 21, 2015 entitled "Pharmaceutical Compositions Comprising Gels and Methods for Fabricating Thereof", which claims priority under 35 U.S.C. § 119(e) to U.S. Provisional Application No. 62/002,711 filed on May 23, 2014 entitled "Pharmaceutical Compositions Comprising Gels and Methods for Fabricating Thereof"; the entire contents of each is herein incorporated by reference.

FIELD OF THE INVENTION

The present invention relates generally to the pharmaceutical field of and more specifically to compositions comprising gels based on thermoreversible polymers and to methods of preparing and using such compositions.

BACKGROUND

In ophthalmological treatments and procedures, many typical ophthalmic drug delivery systems encounter difficulties and problems due to physiological conditions of the eye. More specifically, when a liquid ophthalmic formulation is applied to the eye, upon instillation, it is quickly eliminated due to lacrimal secretion and drainage. As a result, only a limited number of ophthalmic drugs can be utilized by patients to achieve efficient treatment; otherwise a frequent administration of concentrated solutions is often required to achieve the desired effects. It naturally follows that increasing the retention time of a liquid ophthalmic formulation after it has been administered is often very desirable. Similarly, the same is desirable for topical drug formulations that are applied to skin of burn patients to relieve the burn symptoms and to accelerate the process of healing or gun-shot victims to seal wound and prevent loss of blood.

In the field of ophthalmology, to lengthen the retention time of instilled drug in the eye and to enhance its bioavailability, various ophthalmic vehicles, such as ointments, aqueous gels, suspensions inserts and implants, have been developed and used. However, these ophthalmic vehicles are not free of flaws and drawbacks. For example, the use of ointments often causes blurred vision. Using inserts caused serious problems due to low patient compliance. Implants require surgical intervention with concomitant risks of infection and inflammation.

Gel forming systems have been especially popular for increasing the pre-corneal retention time and improving bioavailability of the ophthalmic drugs. Typically, such gels comprise thermoreversible polymers that can undergo a rapid liquid-to-gel phase transition once they have been administered to the eye. However, typical in situ gel-forming compositions require the use of high concentrations of polymer to form the gel and therefore typically are not suitable for use in ophthalmic drug delivery.

This patent specification discloses alternative in situ gel-forming compositions that are free of the above described drawbacks and deficiencies making them better suitable for both ophthalmological and burn-healing treatments, and methods of fabricating and administering the same.

SUMMARY

According to one embodiment of the invention, a pharmaceutical ophthalmological composition or a composition for treating burns is provided, the composition comprising a therapeutically effective quantity of an active component that is free of any of fluconazole, methazolamide, azitromycin, mitomycin, pilocarpine, povidone-iodine, dexamethasone, flurbiprofen, bromfenac, nepafenac, diclofenac, ketorolac, indomethacin, suprofen, norfloxacin, ciprofloxacin, antiseptics comprising the $NH_4^+$ cation or pharmaceutically acceptable isomers, salts, hydrates or solvates thereof; and a quantity of a thermoreversible gel component that is free of any of chitosan, carbopol or polysorbate.

According to another embodiment of the invention, the active component of the pharmaceutical ophthalmological composition comprises at least one anesthetic, at least one non-steroid anti-inflammatory drug (NSAID), at least one anti-bacterial agent, at least one antiviral medicament, at least one antifungal medicament, at least one immunosuppressant, at least one corticosteroid, at least one keratopathy agent, at least one antioxidant, at least one vitamin, at least one medicament for treating glaucoma, at least one mydriatic agent, at least one antihistamine agent, at least one anti-VEGF medicament, at least one medicament for corneal pain treatment or at least one medicament for severe dry eye syndrome treatment.

According to other embodiments of the invention, an ophthalmological pharmaceutical composition is provided, the composition comprising a therapeutically effective quantity of an corticosteroid selected from the group consisting of triamcinolone, dexamethasone, betamethasone, fluorometholone, fluocinolone, prednisone, prednisolone, hydrocortisone and combinations thereof; a therapeutically effective quantity of an anti-bacterial agent selected from the group consisting of moxifloxacin, gatifloxacin, nalidixic acid, oxolinic acid, piromidic acid, pipemidic acid, rosoxacin, enoxacin, fleroxacin, lomefloxacin, nadifloxacin, ofloxacin, pefloxacin, rufloxacin, balofloxacin, levofloxacin, pazufloxacin, sparfloxacin, tosufloxacin, clinafloxacin, gemifloxacin, sitafloxacin, prulifloxacin and combinations thereof; and a quantity of a thermoreversible gel component comprising a polymer selected from the group consisting of poly(oxyethylene-co-oxypropylene) block copolymer, poly (N-isopropylacrylamide), poly(N-isopropylacrylamide-co-acrylic acid), poly(vinyl pyrrolidone), poly(4-vinylpyridine-co-ethylacrylate) block copolymer, poly(N-isopropylacrylamide-co-butyl methacrylate-co-ethylene glycol) block copolymer and combinations thereof.

According to yet another embodiment of the invention, the active component of the pharmaceutical composition for treating burns comprises at least one anesthetic, at least one non-steroid anti-inflammatory drug, at least one anti-bacterial agent, at least one antifungal medicament, at least one burn-healing agent or at least one medicament for treating neuropathic pain.

Examples of suitable specific active components as well as concentrations thereof are further provided herein, for both ophthalmological compositions and compositions for treating burns.

According to another embodiment of the invention, the gel component of pharmaceutical compositions described herein includes thermoreversible polymer(s), for example, poly(oxyethylene-co-oxypropylene) block copolymer, such as Poloxamer 407®, including thermoreversible polymers having cross-linked portion(s).

According to yet another embodiment of the invention, the gel component of pharmaceutical compositions described herein is sterile, and methods of sterilization of the gel component are also provided herein.

According to other embodiment of the invention, methods of preparing and using the pharmaceutical compositions are also described herein.

DETAILED DESCRIPTION

A. Terms and Definitions

Unless specific definitions are provided, the nomenclatures utilized in connection with, and the laboratory procedures and techniques of analytical chemistry, synthetic organic and inorganic chemistry described herein, are those known in the art. Standard chemical symbols are used interchangeably with the full names represented by such symbols. Thus, for example, the terms "hydrogen" and "H" are understood to have identical meaning. Standard techniques may be used for chemical syntheses, chemical analyses, formulating compositions and testing them. The foregoing techniques and procedures can be generally performed according to conventional methods well known in the art.

It is to be understood that both the foregoing general description and the following detailed description are exemplary and explanatory only and are not restrictive of the invention claimed. As used herein, the use of the singular includes the plural unless specifically stated otherwise. The section headings used herein are for organizational purposes only and are not to be construed as limiting the subject matter described.

As used herein, "or" means "and/or" unless stated otherwise. Furthermore, use of the term "including" as well as other forms, such as "includes," and "included," is not limiting.

"About" as used herein means that a number referred to as "about" comprises the recited number plus or minus 1-10% of that recited number. For example, "about" 100 degrees can mean 95-105 degrees or as few as 99-101 degrees depending on the context. Whenever it appears herein, a numerical range such as "1 to 20" refers to each integer in the given range; i.e., meaning only 1, only 2, only 3, etc., up to and including only 20.

The term "pharmaceutical composition" is defined as a chemical or a biological compound or substance, or a mixture or combination of two or more such compounds or substances, intended for use in the medical diagnosis, cure, treatment, or prevention of disease or pathology.

The term "anesthetic" refers to substances or compounds that induce insensitivity to pain such as a temporary loss of sensation.

The term "anti-inflammatory" refers to substances or compounds that counteract or suppress inflammation via any mechanism or route.

The term "non-steroid anti-inflammatory drug" or "NSAID" refer to substances or compounds that are free of steroid moieties and provide analgesic, antipyretic and/or anti-inflammatory effects.

The terms "anti-bacterial," "antibiotic" and "antiseptic" used herein interchangeably, refer to substances or compounds that destroy bacteria and/or inhibit the growth thereof via any mechanism or route.

The term "antiviral" refers to substances or compounds that destroy a virus or suppresses its ability to replicate, multiply and reproduce; accordingly the term "antiviral" for the purposes of the present application is inclusive of viricides.

The term "antifungal" refers to substances or compounds that destroy or prevent the growth of fungi by selectively eliminating fungal pathogens from a host.

The term "immunosuppressant" refers to substances or compounds that are capable of suppressing the immune response of the body that may be otherwise triggered by any disease, condition or pathology.

The term "corticosteroid" is defined as a compound belonging to a sub-genus of steroids that are derivatives of corticosterone, the latter having the chemical structure:

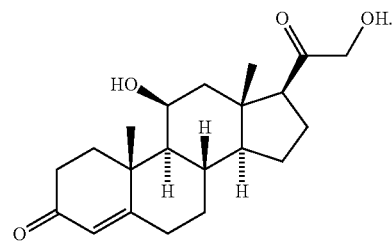

The term "keratopathy agent" refers to substances or compounds that can be used for treating any noninflammatory disease of the cornea, e.g., but not limited to, band keratopathy, acid-fast keratopathy or bullous keratopathy.

The term "antioxidant" refers to substances or compounds that inhibit, eliminate or reduce the damage caused by oxidation, e.g., that caused by free radicals.

The term "mydriatic" refers to substances or compounds that can causing dilation of the pupil of an eye.

The term "antihistamine" refers to substances or compounds that counteract the physiological effects (e.g., allergic reactions) of histamine.

The term "salt" refers to an ionic compound which is a product of the neutralization reaction of an acid and a base.

The terms "solvate" and "hydrate" are used herein to indicate that a compound or a substance is physically or chemically associated with a solvent for "solvates" such as water (for "hydrates").

The term "gel" refers to a solid three-dimensional network that spans the volume of a liquid medium and ensconces this liquid medium.

The terms "thermoreversible" or "thermoreversible gel" for the purposes of the present invention refer to a swollen polymer network formed through the physical aggregation of polymer chains or through thermally reversible glassy domains (e.g., one based on block copolymers), where the product comprising this network is solid, semi-solid or gel like at the room temperature or a higher temperature but is fluid at a temperature that is lower than the room temperature.

The term "block copolymer" refers to macromolecules that comprise two or more homopolymer subunits linked by covalent bond, having at least one structural feature (i.e., an intermediate non-repeating subunit) that is not present in the adjacent portions. For the purposes of the present specification, block copolymers are defined as both linear, branched and partially or fully cross-linked macromolecules.

The term "burn" refers to an injury to skin, tissue or flesh of a mammal caused by heat, flame, electricity, chemical exposure, friction or radiation.

The term "topical medication" refers to substances or compounds that a medication that are applied locally to the skin or mucous membranes of a mammal to treat various diseases or pathologies.

The term "carrier" refers to a substance that serves as a vehicle for improving the efficiency of delivery and the effectiveness of a pharmaceutical composition.

The term "excipient" refers to a pharmacologically inactive substance that is formulated in combination with the pharmacologically active ingredient of pharmaceutical composition and is inclusive of bulking agents, fillers, diluents and products used for facilitating drug absorption or solubility or for other pharmacokinetic considerations.

The term "therapeutically effective amount" is defined as the amount of the compound or pharmaceutical composition that will elicit the biological or medical response of a tissue, system, animal or human that is being sought by the researcher, medical doctor or other clinician.

The term "pharmaceutically acceptable" is defined as a carrier, whether diluent or excipient, that is compatible with the other ingredients of the formulation and not deleterious to the recipient thereof.

The terms "administration of a composition" or "administering a composition" are defined to include an act of providing a compound of the invention or pharmaceutical composition to the subject in need of treatment.

The term "instillation" refers to an introduction of a liquid pharmaceutical composition, such as eye drops, in a drop-by-drop fashion.

The term "intraocular injection" refers to an injection that is administered by entering the eyeball of the patient.

B. Embodiments

According to embodiments of the present invention, pharmaceutical compositions intended to prevent and/or treat ophthalmological diseases, conditions, pathologies or syndromes in mammals, and/or treat burns and/or gun-shot wounds in mammals, are provided, the compositions comprising, consisting essentially of, or consisting of an active component and a gel, and optionally further include one or several pharmaceutically acceptable excipient(s) and one or several pharmaceutically acceptable carrier(s).

It is provided that the same or different gel component(s) may be present in the pharmaceutical compositions for both ophthalmological and burn-treating applications, with no limitations other than the gel component be thermoreversible as further explained below.

With respect to the active component, however, it is provided in some embodiments that, for both ophthalmological and burn-treating applications, certain compounds are specifically excluded ("excluded compounds") from the active component of the composition. Such excluded compounds are fluconazole, methazolamide, azitromycin, mitomycin, pilocarpine, povidone-iodine, dexamethasone, flurbiprofen, bromfenac, nepafenac, diclofenac, ketorolac, indomethacin, suprofen, norfloxacin, ciprofloxacin, antiseptics comprising the $NH_4^+$ cation or pharmaceutically acceptable isomers, salts, hydrates or solvates thereof, and therefore in these embodiments the compositions of the present invention are free of any of them.

This limitation, however, is intended to convey the meaning that each excluded compound, and any combination thereof, cannot be used only if no other compound (i.e., no compound that is not on this list) is present in the active component of the composition. If other, non-excluded compounds are present, then compounds that are otherwise excluded can be also used.

In other words, the excluded compounds mentioned above, can be still included in the active component of the composition so long as other compounds are also present in the active component composition. For example, dexamethasone is specifically excluded above. However, the active component of the composition may still include dexamethasone if at least one of an anti-bacterial agent(s) such as moxifloxacin, gatifloxacin, nalidixic acid, oxolinic acid, piromidic acid, pipemidic acid, rosoxacin, enoxacin, fleroxacin, lomefloxacin, nadifloxacin, ofloxacin, pefloxacin, rufloxacin, balofloxacin, levofloxacin, pazufloxacin, sparfloxacin, tosufloxacin, clinafloxacin, gemifloxacin, sitafloxacin or prulifloxacin is also a part of the active component of the composition.

Similarly, bromfenac, nepafenac, diclofenac and ketorolac are NSAID's that are specifically excluded can still be used in combination with other compounds in the active component of the composition. For instance, bromfenac, nepafenac, diclofenac or ketorolac can still be used in combination with one or more corticosteroid(s) (e.g., triamcinolone, dexamethasone, betamethasone, fluorometholone, fluocinolone, prednisone, prednisolone or hydrocortisone) and/or with one or more anti-bacterial agent(s) (e.g., moxifloxacin, gatifloxacin, nalidixic acid, oxolinic acid, piromidic acid, pipemidic acid, rosoxacin, enoxacin, fleroxacin, lomefloxacin, nadifloxacin, ofloxacin, pefloxacin, rufloxacin, balofloxacin, levofloxacin, pazufloxacin, sparfloxacin, tosufloxacin, clinafloxacin, gemifloxacin, sitafloxacin or prulifloxacin).

Any other compounds may be used in the active component and the compounds as well as the active component as a whole may be the same or different for ophthalmological and burn-treating applications, as further explained below.

Ophthalmological Pharmaceutical Compositions.

For ophthalmological applications, the compositions include at least one active component comprising, consisting essentially of, or consisting of a therapeutically effective quantity of any of the following, or any combination thereof:

(a) at least one anesthetic; and/or
(b) at least one non-steroid anti-inflammatory drug (NSAID); and/or
(c) at least one anti-bacterial agent (i.e., an antibiotic or antiseptic); and/or
(d) at least one antiviral medicament; and/or
(e) at least one antifungal medicament; and/or
(f) at least one immunosuppressant;
(g) at least one corticosteroid; and/or
(h) at least one keratopathy agent; and/or
(i) at least one antioxidant; and/or
(j) at least one vitamin; and/or
(k) at least one medicament for treating glaucoma; and/or
(l) at least one mydriatic agent; and/or
(m) at least one antihistamine agent; and/or
(n) at least one anti-VEGF (i.e., vascular endothelial growth factor) medicament;
(o) at least one medicament for corneal pain treatment and/or
(p) at least one medicament for severe dry eye syndrome treatment.

Any ophthalmological pharmaceutical composition may be formulated that includes at least one or possibly several or all active components (a)-(p) listed above. One having ordinary skill in the art will determine, taking into account medical, pharmaceutical and other requirements and limitations, which active components are to be used depending on the kind of disease, disorder, pathology or syndrome that the ophthalmological pharmaceutical composition is intended for treating. For example, the composition may include one or several antibiotics and one or several corticosteroids and no further active ingredients, or may in addition contain other active components, as desired. The following general guidelines may be followed when determining what specific active components may be used and at which concentrations.

The concentration of the anesthetic(s) in the ophthalmological compositions of the present application may be between about 0.01 mg/mL and about 100.0 mg/mL, such as between about 5.0 mg/mL and about 50.0 mg/mL, for example, about 25.0 mg/mL. Non-limiting examples of the anesthetics that may be utilized include lidocaine, tetracaine, proparacaine, procaine, dyclonine and combinations thereof.

The concentration of the non-steroid anti-inflammatory drug(s) in the ophthalmological compositions of the present application may be between about 0.1 mg/mL and about 100.0 mg/mL, such as between about 5.0 mg/mL and about 50.0 mg/mL, for example, about 15.0 mg/mL. Non-limiting examples of the NSAIDs that may be utilized include ketoprofen, ibuprofen and combinations thereof.

The concentration of the anti-bacterial agent(s) in the ophthalmological compositions of the present application may be between about 0.01 mg/mL and about 50.0 mg/mL, such as between about 0.5 mg/mL and about 10.0 mg/mL, for example, about 1.0 mg/mL. Non-limiting examples of the anti-bacterial agents that may be used include fluoroquinolones other than those specifically excluded above, such, as, for example, moxifloxacin, gatifloxacin, nalidixic acid, oxolinic acid, piromidic acid, pipemidic acid, rosoxacin, enoxacin, fleroxacin, lomefloxacin, nadifloxacin, ofloxacin, pefloxacin, rufloxacin, balofloxacin, levofloxacin, pazufloxacin, sparfloxacin, tosufloxacin, clinafloxacin, gemifloxacin, sitafloxacin, prulifloxacin and combinations thereof. Non-limiting examples of anti-bacterial agents other than fluoroquinolones that may be used include vancomycin, teicoplanin, televancin, decaplanin, ramoplanin, gentamicin, tobramycin, amikacin, cefuroxime, neomycin, neosporin, amoebicides (e.g., metronidazole, tinidazole, secnidazole, ornidazole, polyhexamethylene biguanide or chlorohexidine), polymyxin, clindamycin, bacitracin, chloramphenicol, erythromycin, natamycin, blephamide, sulfacetamide, sodium bicarbonate and combinations thereof.

The concentration of the antiviral medicament(s) in the ophthalmological compositions of the present application may be between about 0.01 mg/mL and about 75.0 mg/mL, such as between about 1 mg/mL and about 50.0 mg/mL, for example, about 20.0 mg/mL. Non-limiting examples of the antiviral medicaments that may be used include idoxuridine, vidarabine and combinations thereof.

The concentration of the antifungal medicament(s) in the ophthalmological compositions of the present application may be between about 0.01 mg/mL and about 75.0 mg/mL, such as between about 1 mg/mL and about 50.0 mg/mL, for example, about 20.0 mg/mL. One non-limiting example of the antifungal medicament that may be used is ketoconazole.

The concentration of the immunosuppressant(s) in the ophthalmological compositions of the present application may be between about 0.01 mg/mL and about 50.0 mg/mL, such as between about 0.1 mg/mL and about 30.0 mg/mL, for example, about 20.0 mg/mL. Non-limiting examples of the immunosuppressants that may be used include tacrolimus, cyclosporine and combinations thereof.

The concentration of the corticosteroid(s) in the ophthalmological compositions of the present application may be between about 0.01 mg/mL and about 50.0 mg/mL, such as between about 0.1 mg/mL and about 40.0 mg/mL, for example, about 25.0 mg/mL. Non-limiting examples of the corticosteroids that may be used include triamcinolone, betamethasone, dexamethasone fluorometholone, fluocinolone, prednisone, prednisolone, hydrocortisone and combinations thereof.

The concentration of the keratopathy agent(s) in the ophthalmological compositions of the present application may be between about 0.01 mg/mL and about 100.0 mg/mL, such as between about 0.1 mg/mL and about 75.0 mg/mL, for example, about 30.0 mg/mL. One non-limiting example of the keratopathy agent that may be used is ethylenediaminetetraacetic acid.

The concentration of the antioxidant(s) in the ophthalmological compositions of the present application may be between about 0.1 mg/mL and about 200.0 mg/mL, such as between about 1.0 mg/mL and about 100.0 mg/mL, for example, about 50.0 mg/mL. Non-limiting examples of the antioxidants that may be used include acetylcysteine, glutathione and combinations thereof.

The concentration of the vitamin(s) in the ophthalmological compositions of the present application may be between about 0.1 mg/mL and about 100.0 mg/mL, such as between about 1.0 mg/mL and about 50.0 mg/mL, for example, about 5.0 mg/mL. One non-limiting example of the vitamin that may be used is riboflavin.

The concentration of the medicament(s) for treating glaucoma in the ophthalmological compositions of the present application may be between about 0.1 mg/mL and about 100.0 mg/mL, such as between about 1.0 mg/mL and about 50.0 mg/mL, for example, about 25.0 mg/mL. Non-limiting examples of the medicaments for treating glaucoma that may be used include of bimatoprost, latanoprost, travoprost, apraclonidine, brimonidine, dipivefrin, physostigmine, betoxolol, timolol, carbachol, acetazolamide and combinations thereof.

The concentration of the mydriatic agent(s) in the ophthalmological compositions of the present application may be between about 0.001 and about 0.5 mass %, such as between about 0.01 and about 0.3 mass %, for example, between about 0.03 and about 0.1 mass %. Non-limiting examples of the mydriatic agents that may be used include epinephrine, phenylephrine, tropicamide and combinations thereof.

The concentration of the antihistamine agent(s) in the ophthalmological compositions of the present application may be between about 0.1 mg/mL and about 100.0 mg/mL, such as between about 1.0 mg/mL and about 50.0 mg/mL, for example, about 25.0 mg/mL. Non-limiting example of the antihistamine agents that may be used is olopatadine, ketotifen fumarate and combinations thereof.

The concentration of the anti-VEGF medicament(s) in the ophthalmological compositions of the present application may be between about 0.1 mg/mL and about 100.0 mg/mL, such as between about 1.0 mg/mL and about 50.0 mg/mL, for example, about 2.0 mg/mL. Non-limiting examples of the anti-VEGF medicaments that may be used include bevacizumab, pegaptanib, ranibizumab, lapatinib, sunitinib, sorafenib, axitinib, pazopanib and combinations thereof.

The concentration of the medicament(s) for corneal pain treatment in the ophthalmological compositions of the present application may be between about 0.1 mg/mL and about 100.0 mg/mL, such as between about 1.0 mg/mL and about 50 mg/mL, for example, about 25.0 mg/mL. Non-limiting examples of the medicaments for corneal pain treatment that may be used include nalbuphine, morphine and other opioids and combinations thereof.

The concentration of the medicament(s) for severe dry eye syndrome treatment in the ophthalmological compositions of the present application may be between about 0.1 mg/mL and about 100.0 mg/mL, such as between about 1.0 mg/mL and about 50.0 mg/mL, for example, about 20.0 mg/mL. Non-limiting examples of the medicament(s) for severe dry eye syndrome treatment that may be used include albumin, plasminogen and combinations thereof.

Those having ordinary skill in the art can determine the optimal concentration for each specific active component that is used, based on medical pharmaceutical and other considerations that are commonly taken into account.

Pharmaceutical Compositions for Treating Burns.

For burn-treating applications, and in some embodiments, for applications intended to treat gun-shot wounds, the compositions include an active component comprising, consisting essentially of, or consisting of a therapeutically effective quantity of any of the following, or any combination thereof:

(a) at least one anesthetic; and/or
(b) at least one non-steroid anti-inflammatory drug (NSAID); and/or
(c) at least one anti-bacterial agent (i.e., an antibiotic or an antiseptic); and/or
(d) at least one antifungal agent; and/or
(e) at least one burn-healing agent; and/or
(f) at least one medicament for treating neuropathic pain.

The concentration of the anesthetic(s) in the burn-treating compositions of the present application may be between about 0.01 mg/mL and about 250.0 mg/mL, such as between about 1.0 mg/mL and about 100.0 mg/mL, for example, about 50.0 mg/mL. Non-limiting examples of the anesthetics that may be utilized include lidocaine, tetracaine, proparacaine, procaine, dyclonine and combinations thereof.

The concentration of the non-steroid anti-inflammatory drug(s) in the burn-treating compositions of the present application may be between about 0.1 mg/mL and about 100.0 mg/mL, such as between about 5.0 mg/mL and about 50.0 mg/mL, for example, about 25.0 mg/mL. Non-limiting examples of the NSAIDs that may be utilized include ketoprofen, ibuprofen and combinations thereof.

The concentration of the anti-bacterial agent(s) in the burn-treating compositions of the present application may be between about 0.01 mg/mL and about 100.0 mg/mL, such as between about 0.5 mg/mL and about 75 mg/mL, for example, about 10.0 mg/mL. Non-limiting examples of the anti-bacterial agents that may be used include fluoroquinolones (other than those specifically excluded as stated above), vancomycin, moxifloxacin, gatifloxacin, teicoplanin, telavancin, decaplanin, ramoplanin, gentamicin, tobramycin, amikacin, cefuroxime, neomycin, neosporin, amoebicides (e.g., metronidazole, tinidazole, secnidazole, ornidazole, polyhexamethylene biguanide or chlorohexidine), polymyxin, clindamycin, bacitracin, chloramphenicol, erythromycin, natamycin, blephamide, sulfacetamide, sodium bicarbonate and combinations thereof.

The concentration of the antifungal medicament(s) in the burn-treating compositions of the present application may be between about 0.01 mg/mL and about 75.0 mg/mL, such as between about 1.0 mg/mL and about 50.0 mg/mL, for example, about 20.0 mg/mL. One non-limiting example of the antifungal medicament that may be used is ketoconazole.

The concentration of the burn healing agent(s) in the burn-treating compositions of the present application may be between about 0.025 mg/mL and about 10.0 mg/mL, such as between about 0.25 mg/mL and about 5.0 mg/mL, for example, about 1.0 mg/mL. One non-limiting example of the burn healing agent that may be utilized is misoprostol.

The concentration of the medicament(s) for treating neuropathic pain in the burn-treating compositions of the present application may be between about 0.1 mg/mL and about 100.0 mg/mL, such as between about 1.0 mg/mL and about 75.0 mg/mL, for example, about 50.0 mg/mL. Non-limiting examples of the medicaments for treating neuropathic pain that may be used include ketamine, morphine, fentanyl, pregabalin, carbamazepine, gabapentin, clonidine and combinations thereof.

Again, the same as for the ophthalmological compositions, those having ordinary skill in the art can determine the optimal concentration for each specific active component that is used in the burn-treating compositions, based on medical pharmaceutical and other considerations that are commonly taken into account.

As stated above, all the compositions of the present invention, both for ophthalmological and burn-treating applications, include a gel. A typical gel that is useful for the purposes of the present invention is a thermoreversible gel as defined above, i.e., being in a solid or gel-like state at a room temperature of about 20° C. or higher and being in a fluid state at lower temperatures, such as having the value of dynamic viscosity of about 10 centipoise or less, such as about 1.3 centipoise or less. To form a thermoreversible gel, a suitable thermoreversible polymer is combined with water. A concentration of the polymer in water may be between about 1.0 mg/mL and about 500.0 mg/mL, such as between about 50.0 mg/mL and about 350.0 mg/mL, for example, about 200.0 mg/mL.

A variety of polymers can be used for forming a thermoreversible gel. Those skilled in the art will select polymers and their concentrations that are most appropriate. Some non-limiting examples of such polymers include poly(oxyethylene-co-oxypropylene) block copolymers, poly(N-isopropylacrylamide), poly(N-isopropylacrylamide-co-acrylic acid), poly(vinyl pyrrolidone), poly(4-vinylpyridine-co-ethylacrylate) block copolymers and poly(N-isopropylacrylamide-co-butyl methacrylate-co-ethylene glycol) block copolymers. Such block copolymers may include cross-linked portions.

According to one non-limiting embodiment, a reversible gel-forming polymer that can be used is a non-ionic poly(oxyethylene-co-oxypropylene) block copolymer having the following general structure:

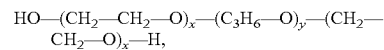

wherein in some further non-limiting embodiments, x is an integer that can have the value of at least 8 and y is an integer that can have the value of at least 38.

One non-limiting example of an even more specific non-ionic poly(oxyethylene-co-oxypropylene) block copolymer that can be used is the product known under the trade name Poloxamer 407® (poly(ethylene glycol)-block-poly(propylene glycol)-block-poly(ethylene glycol)) available from Sigma-Aldrich Corp. of St. Louis, Mo. (the trade name is owned by BASF Corp.), with the molecular weight of the polyoxypropylene portion of about 4,000 Daltons, about a 70% polyoxyethylene content, the overall molecular weight of between about 9,840 Daltons and about 14,600 Daltons and having the following chemical structure

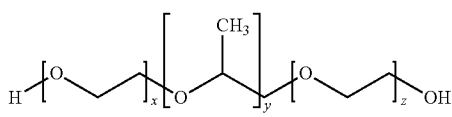

wherein each x and z is an integer having the value between about 78 and about 116, and y is an integer having the value of about 69.

Other similar products of the Poloxamer® family are useful for forming the thermoreversible gel of the compositions of the present invention are, for example, the products of the Pluronic® family, Kolliphor® family (the trade names are also owned by BASF) or Synperonics® family (Croda International plc). Any polymer of Poloxamer®, Pluronic®, Kolliphor® or Synperonics® family that is used may contain any portion that is cross-linked.

According to further embodiments, methods for fabricating the above-described pharmaceutical compositions are provided. In one embodiment, the thermoreversible gel can be prepared first followed by adding a pre-determined quantity of an active component, or vice versa. If more than one active component is to be used, the active component(s) may be added to the thermoreversible gel in any order to be selected by one of ordinary skill in the art and may be added either simultaneously or consecutively, or be pre-mixed first followed by adding the mixture to the gel component.

In one exemplary, non-limiting procedure, a sterile thermoreversible gel is prepared first, for example, by combining a suitable thermoreversible polymer with sterile water followed by further sterilization of the resulting gel, for example by autoclaving, treatment by gamma-radiation or by exposing it to a flow of ethylene oxide. Those having ordinary skill in the art can determine which sterilization method is best suited in a particular procedure.

For example, if a standard autoclaving method of sterilization is to be used, the thermoreversible gel prepared as described above can be subjected to a temperature between about 200° C. and about 300° C., e.g., about 250° C., for about 30 to 40 minutes at a pressure of about 30 bars (i.e., about 29.6 atm or 3 MPa) in a standard autoclaving apparatus. The sterilized gel can be then dispensed into a suitable container (e.g., a sterile ophthalmic dropper bottle or, alternatively, a sterile vial or a sterile syringe, if desired). A complete testing for sterility and the presence of endotoxin in the gel may be performed according to commonly used methods known to those having ordinary skill in the art. A sterile thermoreversible gel that is prepared by any sterilization method disclosed above can then be used to fabricate a pharmaceutical composition.

To prepare a pharmaceutical composition, a sterile thermoreversible gel prepared as described above is to be combined with a selected active component by any acceptable mixing method; for example, the gel and the active component may be mixed in a single sterile container such as an ophthalmic dropper bottle, a sterile vial or a syringe and such quantities of the gel and the active component are to be selected as to achieve a desired, pre-determined concentration of the active component in the overall composition, as disclosed above.

In one, non-limiting specific embodiment, a pharmaceutical composition formulated for delivery as topical ophthalmic drops can be prepared, the composition comprising an active component that includes therapeutically effective quantities of a corticosteroid such as triamcinolone and of an anti-bacterial agent such as moxifloxacin. The composition can be prepared by combining this active component with a quantity of pre-sterilized gel, based, for example, on Poloxamer 407®.

Pharmaceutical compositions prepared as described above can be used for treating any disease, complication, pathology or syndrome that the active component is intended to treat. Typically, a pharmaceutical composition described above will be administered to a mammalian subject (e.g., humans, cats, dogs, other pets, domestic, wild or farm animals) in need of emergent, urgent or planned ophthalmic treatment or, alternatively, in need of a burn treatment or a gun-shot wound treatment.

A pharmaceutical composition described above can be delivered in a variety of ways, such as, for ophthalmic applications, topical ophthalmic drops, eye sprays or they can be injected (e.g., via subconjunctival injection) using methods and techniques known to those having ordinary skilled in the art of ophthalmology. The composition at the pre-delivery stage (i.e., at a point of time that is immediately preceding the administration) is cool (i.e., below the room temperature) and is, therefore, a fluid. Following the act of administering the composition, as the composition arrives to the cul-de-sac or a surface of the patient's eye (for ophthalmic compositions), its temperature rapidly rises to that of the body of the patient to whom it is being administered, and becomes gel-like within seconds.

Similarly, for burn gun-shot wound treatments, when a composition is delivered and topically applied to the site of burn or gun-shot wound, its temperature rises to that of the body of the patient whose burns gun-shot wounds are being treated, and quickly gels up upon reaching the body temperature.

It will be understood by those having ordinary skill in the art that the specific dose level and frequency of dosage for any particular patient may be varied and will depend upon a variety of factors including the activity of the specific compound employed, the metabolic stability and length of action of that compound, the age, body weight, general health, gender, diet, and the severity of the particular ophthalmological or burn condition being treated.

In additional embodiments, pharmaceutical kits are provided. The kit includes a sealed sterile container approved for the storage of pharmaceutical compositions, the container containing a sterile gel prepared as described above. An instruction is to be included in the kit providing directions on how to prepare a mixture of the sterile gel with one or more active compounds to make a pharmaceutical composition. Further instructions on how to use the composition may be further provided.

The following examples are provided to further elucidate the advantages and features of the present invention, but are not intended to limit the scope of the invention. The examples are for the illustrative purposes only. USP pharmaceutical grade products were used in preparing the formulations described below.

C. Examples

Example 1. Preparing a Sterile Thermoreversible Gel

A thermoreversible gel was prepared as described below. The following products were used in the amounts specified:
(a) about 20.0 g of Pluronic F127® NF (Poloxamer 407®); and
(b) about 100.0 mL of sterile water, The solution of Pluronic F127® NF was placed into a vessel, then refrigerated water was added. The mixture was kept refrigerated for at least about 12 hours to allow the mixture to become a solution. The thermoreversible gel so obtained was sterilized. To sterilize the gel, it was placed into an autoclaving apparatus and subjected to a temperature of about 300° C., for about 40 minutes at a pressure of about 30 bars. The sterilized gel was then dispensed into an ophthalmic dropper bottle and tested for sterility and the presence of endotoxin. The final product can then be used as a stock solution for preparing a pharmaceutical formulation.

Example 2. Preparing an Ophthalmic Pharmaceutical Composition

A pharmaceutical composition can be prepared as described below. A pre-determined quantity of an active component can be mixed with a pre-determined quantity of the sterilized poloxamer-based gel obtained as described in Example 1.

About 9.0 mL of 20% sterile poloxamer can be placed in a pre-sterilized dropper. About 1.0 mL of a concentrated vancomycin solution, at about 250.0 mg/mL, can be filtered into droptainer and shaken inside hood. Final resultant concentration can, therefore, be about 25.0 mg/mL vancomycin, in about 10.0 mL sterile gel. The composition is to be kept refrigerated until use.

Example 3. Preparing a Topical Pharmaceutical Composition for Treating Burns

A pharmaceutical composition can be prepared as described below. A pre-determined quantity of an active component can be mixed with a pre-determined quantity of the sterilized poloxamer-based gel obtained as described in Example 1.

About 950.0 mL of 20% sterile poloxamer can be placed in a pre-sterilized 1.0 L bottle. Concentrated medications such as about 25.0 mL gentamicin at about 40.0 mg/mL can be added, filtered to the sterile gel and mixed well. Final concentration can, therefore, be about 1 mg/ml gentamicin, still leaving room for addition of up to about 25.0 mL diluent or another medication such as lidocaine, if desired. The composition is to be kept refrigerated until use.

Although the invention has been described with reference to the above examples, it will be understood that modifications and variations are encompassed within the spirit and scope of the invention. Accordingly, the invention is limited only by the following claims.

What is claimed is:

1. An ophthalmological pharmaceutical composition consisting of a quantity of timolol, a quantity of latanaprost and a quantity of poly(oxyethylene-co-oxypropylene) block copolymer in concentration between about 1.0 mg/mL and about 150.0 mg/mL, wherein the composition is a gel at a temperature that is at least about human body temperature and is a fluid at a temperature that is lower than about the body temperature.

2. The ophthalmological pharmaceutical composition of claim 1, wherein the concentration of timolol and latanaprost in the composition is between about 0.1 mg/mL and about 100.0 mg/mL.

3. The ophthalmological pharmaceutical composition of claim 2, wherein the concentration of timolol and latanaprost in the composition is between about 1.0 mg/mL and 50.0 mg/mL.

4. The ophthalmological pharmaceutical composition of claim 3, wherein the concentration of timolol and latanaprost in the composition is about 25.0 mg/mL.

5. An ophthalmological pharmaceutical composition consisting of a quantity of timolol, a quantity of latanaprost and a quantity of poly(oxyethylene-co-oxypropylene) block copolymer in concentration between about 1.0 mg/mL and about 150.0 mg/mL, and a quantity of a second polymer selected from the group consisting of poly(N-isopropylacrylamide), poly(N-isopropylacrylamide-co-acrylic acid), poly (vinyl pyrrolidone), poly(4-vinylpyridine-co-ethylacrylate) block copolymer, poly(N-isopropylacrylamide-co-butyl methacrylate-co-ethylene glycol) block copolymer and combinations thereof, wherein the composition is a gel at a temperature that is at least about human body temperature and is a fluid at a temperature that is lower than about the body temperature.

6. The ophthalmological pharmaceutical composition of claim 5, wherein the concentration of timolol and latanaprost in the composition is between about 0.1 mg/mL and about 100.0 mg/mL.

7. The ophthalmological pharmaceutical composition of claim 6, wherein the concentration of timolol and latanaprost in the composition is between about 1.0 mg/mL and 50.0 mg/mL.

8. The ophthalmological pharmaceutical composition of claim 7, wherein the concentration of timolol and latanaprost in the composition is about 25.0 mg/mL.

* * * * *